United States Patent
McCaffrey et al.

(10) Patent No.: US 10,130,269 B2
(45) Date of Patent: Nov. 20, 2018

(54) DUAL LUMEN CATHETER FOR PROVIDING A VASCULAR PRESSURE MEASUREMENT

(71) Applicant: Medtronic Vascular Galway, Ballybrit, Galway (IE)

(72) Inventors: Gerry McCaffrey, Ballybrit (IE); Fiachra Sweeney, Ballybrit (IE); Barry O'Connell, Ballybrit (IE); Christopher Murphy, Ballybrit (IE)

(73) Assignee: MEDTRONIC VASCULAR, INC, Santa Rosa, CA (US)

( * ) Notice: Subject to any disclaimer, the term of this patent is extended or adjusted under 35 U.S.C. 154(b) by 860 days.

(21) Appl. No.: 14/080,484

(22) Filed: Nov. 14, 2013

(65) Prior Publication Data

US 2015/0133800 A1    May 14, 2015

(51) Int. Cl.
*A61B 5/02* (2006.01)
*A61B 5/0215* (2006.01)
(Continued)

(52) U.S. Cl.
CPC .......... *A61B 5/0215* (2013.01); *A61B 5/6852* (2013.01); *A61M 25/00* (2013.01);
(Continued)

(58) Field of Classification Search
CPC .......... A61B 5/0215; A61B 2562/0247; A61B 5/6852; A61M 2025/0002; A61M 2025/0003; A61M 25/00
See application file for complete search history.

(56) References Cited

U.S. PATENT DOCUMENTS

| 4,718,425 A | 1/1988 | Tanaka et al. |
| 4,771,782 A | 9/1988 | Millar |

(Continued)

FOREIGN PATENT DOCUMENTS

| DE | 102008045878 | 3/2010 |
| EP | 0263190 | 10/1986 |

(Continued)

OTHER PUBLICATIONS

PCT/US2014/064991, PCT International Search Report and the Written Opinion, dated Jan. 23, 2015.

*Primary Examiner* — Puya Agahi
(74) *Attorney, Agent, or Firm* — Medler Ferro Woodhouse & Mills

(57) ABSTRACT

A catheter is disclosed for providing a pressure measurement at a vascular lesion. The catheter includes a tubular component having dual lumens along at least a segment thereof in which a first lumen acts as a pressure inlet and a second lumen allows the catheter to be tracked over a guidewire. A plurality of openings are located along a distal segment of the tubular component that permit blood flow into the first lumen when disposed in vivo. A pressure sensor is located within a handle component of the catheter or within the tubular component to be in fluid communication with a proximal end of the first lumen. When the catheter is positioned at the vascular lesion, the first lumen fills with blood via the plurality of openings such that the pressure sensor is able to sense a pressure of the blood at a distal end of the catheter.

9 Claims, 10 Drawing Sheets

(51) Int. Cl.
*A61B 5/00* (2006.01)
*A61M 25/00* (2006.01)
*A61B 5/03* (2006.01)
*A61B 5/021* (2006.01)

(52) U.S. Cl.
CPC ............ *A61B 5/02* (2013.01); *A61B 5/021* (2013.01); *A61B 5/02007* (2013.01); *A61B 5/03* (2013.01); *A61B 2562/0247* (2013.01); *A61M 2025/0003* (2013.01)

(56) References Cited

U.S. PATENT DOCUMENTS

| | | |
|---|---|---|
| 4,796,641 A | 1/1989 | Mills et al. |
| 4,815,472 A | 3/1989 | Wise et al. |
| 4,850,358 A | 7/1989 | Millar |
| 4,901,731 A | 2/1990 | Millar |
| 4,924,877 A | 5/1990 | Brooks |
| 4,928,693 A | 5/1990 | Goodin et al. |
| 4,936,310 A | 6/1990 | Engstrom et al. |
| 4,941,473 A | 7/1990 | Tenerz et al. |
| 4,966,148 A | 10/1990 | Millar |
| 4,966,156 A | 10/1990 | Perry et al. |
| 5,029,585 A | 7/1991 | Lieber et al. |
| 5,046,497 A | 9/1991 | Millar |
| 5,050,297 A | 9/1991 | Metzger |
| 5,085,223 A | 2/1992 | Lars et al. |
| 5,125,058 A | 6/1992 | Tenerz et al. |
| 5,195,375 A | 3/1993 | Tenerz et al. |
| 5,267,958 A | 12/1993 | Buchbinder et al. |
| 5,280,786 A | 1/1994 | Wlodarczyk et al. |
| 5,427,114 A | 6/1995 | Colliver et al. |
| 5,451,233 A | 9/1995 | Yock |
| 5,466,222 A | 11/1995 | Ressemann et al. |
| 5,526,820 A | 6/1996 | Khoury |
| 5,542,434 A | 8/1996 | Imran et al. |
| 5,564,425 A | 10/1996 | Tonokura |
| 5,569,219 A | 10/1996 | Hakki et al. |
| 5,573,007 A | 11/1996 | Bobo, Sr. |
| 5,591,129 A | 1/1997 | Shoup et al. |
| 5,637,091 A | 6/1997 | Hakky et al. |
| RE35,648 E | 11/1997 | Tenerz et al. |
| 5,694,946 A | 12/1997 | Tenerz et al. |
| 5,701,905 A | 12/1997 | Esch |
| 5,715,827 A | 2/1998 | Corl et al. |
| 5,813,997 A | 9/1998 | Imran et al. |
| 5,827,243 A | 10/1998 | Palestrant et al. |
| 5,873,835 A | 2/1999 | Hastings et al. |
| 5,902,248 A | 5/1999 | Millar et al. |
| 5,964,714 A | 10/1999 | Lafontaine |
| 6,033,366 A | 3/2000 | Brockway et al. |
| 6,056,719 A | 5/2000 | Mickley |
| 6,089,103 A | 7/2000 | Smith |
| 6,106,476 A | 8/2000 | Corl et al. |
| 6,106,486 A | 8/2000 | Tenerz et al. |
| 6,112,598 A | 9/2000 | Tenerz et al. |
| 6,142,958 A | 11/2000 | Hammarstrom et al. |
| 6,167,763 B1 | 1/2001 | Tenerz et al. |
| 6,179,856 B1 * | 1/2001 | Barbere ............ A61M 25/1006 604/97.02 |
| 6,182,513 B1 | 2/2001 | Stemme et al. |
| 6,193,669 B1 | 2/2001 | Degany et al. |
| 6,224,585 B1 | 5/2001 | Pfeiffer |
| 6,248,083 B1 | 6/2001 | Smith et al. |
| 6,296,615 B1 | 10/2001 | Brockway et al. |
| 6,312,380 B1 | 11/2001 | Hoek et al. |
| 6,336,906 B1 | 1/2002 | Hammarstrom et al. |
| 6,354,999 B1 | 3/2002 | Dgany et al. |
| 6,379,308 B1 | 4/2002 | Brockway et al. |
| 6,394,986 B1 | 5/2002 | Millar |
| 6,409,677 B1 | 6/2002 | Tulkki |
| 6,471,656 B1 | 10/2002 | Shalman et al. |
| 6,517,481 B2 | 2/2003 | Hoek et al. |
| 6,546,804 B2 | 4/2003 | Stemme et al. |
| 6,551,250 B2 | 4/2003 | Khalil |
| 6,565,514 B2 | 5/2003 | Svanerudh et al. |
| 6,585,660 B2 | 7/2003 | Dorando et al. |
| 6,615,667 B2 | 9/2003 | Smith |
| 6,659,957 B1 | 12/2003 | Vardi et al. |
| 6,659,959 B2 | 12/2003 | Brockway et al. |
| 6,663,570 B2 | 12/2003 | Mott et al. |
| 6,716,178 B1 | 4/2004 | Kilpatrick et al. |
| 6,733,459 B1 | 5/2004 | Atsumi |
| 6,754,608 B2 | 6/2004 | Svanerudh et al. |
| 6,767,327 B1 | 7/2004 | Corl et al. |
| 6,821,287 B1 | 11/2004 | Jang |
| 6,860,851 B2 | 3/2005 | Knudson et al. |
| 6,868,736 B2 | 3/2005 | Sawatari et al. |
| 6,926,674 B2 | 8/2005 | Tenerz et al. |
| 6,938,474 B2 | 9/2005 | Melvangs |
| 6,966,890 B2 | 11/2005 | Coyle et al. |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,017,416 B1 | 3/2006 | Liu et al. |
| 7,021,152 B2 | 4/2006 | Tenerz |
| 7,025,727 B2 | 4/2006 | Brockway et al. |
| 7,060,038 B2 | 6/2006 | Letort et al. |
| 7,097,620 B2 | 8/2006 | Corl et al. |
| 7,112,170 B2 | 9/2006 | Schock et al. |
| 7,134,994 B2 | 11/2006 | Alpert et al. |
| 7,137,953 B2 | 11/2006 | Eigler et al. |
| 7,211,048 B1 | 5/2007 | Najafi et al. |
| 7,222,539 B2 | 5/2007 | Tulkki |
| 7,229,403 B2 | 6/2007 | Schock et al. |
| 7,245,789 B2 | 7/2007 | Bates et al. |
| 7,263,894 B2 | 9/2007 | Tenerz |
| 7,274,956 B2 | 9/2007 | Mott et al. |
| RE39,863 E | 10/2007 | Smith |
| 7,294,117 B2 | 11/2007 | Provost-tine et al. |
| 7,329,223 B1 | 2/2008 | Ainsworth et al. |
| 7,331,236 B2 | 2/2008 | Smith et al. |
| 7,343,811 B2 | 3/2008 | Tenerz et al. |
| 7,347,822 B2 | 3/2008 | Brockway et al. |
| 7,447,388 B2 | 11/2008 | Bates et al. |
| 7,450,989 B2 | 11/2008 | Svanerudh |
| 7,454,244 B2 | 11/2008 | Kassab et al. |
| 7,458,938 B2 | 12/2008 | Patel et al. |
| 7,472,601 B1 | 1/2009 | Tenerz et al. |
| 7,481,774 B2 | 1/2009 | Brockway et al. |
| 7,527,594 B2 | 5/2009 | Vardi et al. |
| 7,532,920 B1 | 5/2009 | Ainsworth et al. |
| 7,599,588 B2 | 10/2009 | Eberle et al. |
| 7,645,233 B2 | 1/2010 | Tulkki et al. |
| 7,660,492 B2 | 2/2010 | Bates et al. |
| 7,724,148 B2 | 5/2010 | Samuelsson et al. |
| 7,731,664 B1 | 6/2010 | Millar |
| 7,775,988 B2 | 8/2010 | Pijls |
| 7,783,338 B2 | 8/2010 | Ainsworth et al. |
| 7,837,650 B1 | 11/2010 | Cox et al. |
| 7,881,573 B2 | 2/2011 | Eberle et al. |
| 7,931,603 B2 | 4/2011 | Von Malmborg et al. |
| 7,946,997 B2 | 5/2011 | Hubinette |
| 7,967,761 B2 | 6/2011 | Smith |
| 7,967,762 B2 | 6/2011 | Corl et al. |
| 7,998,089 B2 | 8/2011 | Smith |
| 8,025,623 B1 | 9/2011 | Millar |
| 8,029,447 B2 | 10/2011 | Kanz et al. |
| 8,059,923 B2 | 11/2011 | Bates et al. |
| 8,140,146 B2 | 3/2012 | Kim et al. |
| 8,157,742 B2 | 4/2012 | Taylor |
| 8,162,856 B2 | 4/2012 | Williams et al. |
| 8,174,395 B2 | 5/2012 | Samuelsson et al. |
| 8,187,195 B2 | 5/2012 | Tulkki |
| 8,216,151 B2 | 7/2012 | Smith |
| 8,231,537 B2 | 7/2012 | Ahmed et al. |
| 8,249,815 B2 | 8/2012 | Taylor |
| 8,277,386 B2 | 10/2012 | Ahmed et al. |
| 8,282,565 B2 | 10/2012 | Mahapatra et al. |
| 8,298,156 B2 | 10/2012 | Manstrom et al. |
| 8,311,747 B2 | 11/2012 | Taylor |
| 8,311,748 B2 | 11/2012 | Taylor et al. |
| 8,311,750 B2 | 11/2012 | Taylor |

(56) References Cited

U.S. PATENT DOCUMENTS

| | | |
|---|---|---|
| 8,315,812 B2 | 11/2012 | Taylor |
| 8,315,813 B2 | 11/2012 | Taylor et al. |
| 8,315,814 B2 | 11/2012 | Taylor et al. |
| 8,317,715 B2 | 11/2012 | Belleville et al. |
| 8,320,723 B2 | 11/2012 | Eberle et al. |
| 8,321,150 B2 | 11/2012 | Taylor |
| 8,410,940 B2 | 4/2013 | Samuelsson et al. |
| 8,419,647 B2 | 4/2013 | Corl et al. |
| 8,419,648 B2 | 4/2013 | Corl et al. |
| 8,461,997 B2 | 6/2013 | Samuelsson et al. |
| 8,485,985 B2 | 7/2013 | Manstrom et al. |
| 8,556,520 B2 | 10/2013 | Elenbaas et al. |
| 8,562,537 B2 | 10/2013 | Alpert et al. |
| 8,636,659 B2 | 1/2014 | Alpert et al. |
| 8,696,584 B2 | 4/2014 | Kassab |
| 8,698,638 B2 | 4/2014 | Samuelsson et al. |
| 8,714,021 B2 | 5/2014 | Gamage |
| 8,797,155 B2 | 8/2014 | Huennekens et al. |
| 8,857,264 B2 | 10/2014 | Gamage |
| 8,958,863 B2 | 2/2015 | Huennekens et al. |
| 8,977,336 B2 | 3/2015 | Huennekens et al. |
| 8,998,823 B2 | 4/2015 | Manstrom et al. |
| 9,011,342 B2 | 4/2015 | Manstrom et al. |
| 9,113,843 B2 | 8/2015 | Manstrom et al. |
| 9,186,072 B2 | 11/2015 | Manstrom et al. |
| 9,220,461 B2 | 12/2015 | Samuelsson et al. |
| 9,259,161 B2 | 2/2016 | Suchecki et al. |
| 9,289,137 B2 | 3/2016 | Corl |
| 9,314,584 B1 | 4/2016 | Riley et al. |
| 9,332,916 B2 | 5/2016 | Kassab |
| 9,339,348 B2 | 5/2016 | Davies et al. |
| 2001/0051769 A1 | 12/2001 | Hoek et al. |
| 2002/0013527 A1 | 1/2002 | Hoek et al. |
| 2002/0035331 A1 | 3/2002 | Brockway et al. |
| 2002/0059827 A1 | 5/2002 | Smith |
| 2002/0065472 A1 | 5/2002 | Brockway et al. |
| 2002/0072880 A1 | 6/2002 | Svanerudh et al. |
| 2002/0157473 A1 | 10/2002 | Stemme et al. |
| 2002/0173724 A1 | 11/2002 | Dorando et al. |
| 2003/0018273 A1 | 1/2003 | Corl et al. |
| 2003/0032886 A1 | 2/2003 | Dgany et al. |
| 2003/0033095 A1 | 2/2003 | Svanerudh et al. |
| 2003/0040674 A1 | 2/2003 | Corl et al. |
| 2003/0159518 A1 | 8/2003 | Sawatari et al. |
| 2003/0163052 A1 | 8/2003 | Mott et al. |
| 2003/0176850 A1 | 9/2003 | Melvas |
| 2003/0195428 A1 | 10/2003 | Brockway et al. |
| 2003/0216621 A1 | 11/2003 | Alpert et al. |
| 2004/0067000 A1 | 4/2004 | Bates et al. |
| 2004/0082844 A1 | 4/2004 | Vardi et al. |
| 2004/0082866 A1 | 4/2004 | Mott et al. |
| 2004/0116816 A1 | 6/2004 | Tenerz et al. |
| 2004/0143240 A1* | 7/2004 | Armstrong ............ A61M 25/00 604/528 |
| 2004/0143261 A1 | 7/2004 | Hartley et al. |
| 2004/0157790 A1 | 8/2004 | Herweijer et al. |
| 2004/0162548 A1 | 8/2004 | Reiser |
| 2004/0167385 A1 | 8/2004 | Rioux et al. |
| 2004/0176790 A1 | 9/2004 | Coyle |
| 2004/0230131 A1 | 11/2004 | Kassab et al. |
| 2004/0254442 A1 | 12/2004 | Williams et al. |
| 2005/0000294 A1 | 1/2005 | Tenerz et al. |
| 2005/0011272 A1 | 1/2005 | Tenerz |
| 2005/0043670 A1 | 2/2005 | Rosenberg |
| 2005/0049451 A1 | 3/2005 | Schock et al. |
| 2005/0187487 A1 | 8/2005 | Azizkhan et al. |
| 2005/0268724 A1 | 12/2005 | Tenerz |
| 2005/0268725 A1 | 12/2005 | Tulkki |
| 2006/0052700 A1 | 3/2006 | Svanerudh |
| 2006/0074318 A1 | 4/2006 | Ahmed et al. |
| 2006/0094966 A1 | 5/2006 | Brockway et al. |
| 2006/0094982 A1 | 5/2006 | Corl et al. |
| 2006/0142756 A1 | 6/2006 | Davies et al. |
| 2006/0207335 A1 | 9/2006 | Tenerz et al. |
| 2006/0241505 A1 | 10/2006 | Ahmed et al. |
| 2006/0287569 A1 | 12/2006 | Schock et al. |
| 2007/0060820 A1 | 3/2007 | Lofgren et al. |
| 2007/0060822 A1 | 3/2007 | Alpert et al. |
| 2007/0078352 A1 | 4/2007 | Pijls |
| 2007/0106142 A1 | 5/2007 | Von Malmborg et al. |
| 2007/0106165 A1 | 5/2007 | Tulkki |
| 2007/0116408 A1 | 5/2007 | Eberle et al. |
| 2007/0133925 A1 | 6/2007 | Bates et al. |
| 2007/0135718 A1 | 6/2007 | Corl et al. |
| 2007/0162106 A1 | 7/2007 | Evans et al. |
| 2007/0191717 A1 | 8/2007 | Rosen et al. |
| 2007/0220986 A1 | 9/2007 | Smith et al. |
| 2007/0255144 A1 | 11/2007 | Tulkki et al. |
| 2007/0255145 A1 | 11/2007 | Smith et al. |
| 2008/0077085 A1* | 3/2008 | Eidenschink ......... A61M 25/10 604/96.01 |
| 2008/0119739 A1 | 5/2008 | Vardi et al. |
| 2008/0119758 A1 | 5/2008 | Samuelsson et al. |
| 2008/0132806 A1 | 6/2008 | Smith |
| 2008/0139897 A1 | 6/2008 | Ainsworth et al. |
| 2008/0146993 A1 | 6/2008 | Krishna |
| 2008/0200770 A1 | 8/2008 | Hubinette |
| 2008/0255471 A1 | 10/2008 | Naghavi et al. |
| 2008/0262470 A1* | 10/2008 | Lee ..................... A61M 25/001 604/509 |
| 2008/0269572 A1 | 10/2008 | Kanz et al. |
| 2009/0059727 A1 | 3/2009 | Bates et al. |
| 2009/0082678 A1 | 3/2009 | Smith |
| 2009/0088609 A1 | 4/2009 | Schmitz-Rode et al. |
| 2009/0088650 A1 | 4/2009 | Corl |
| 2009/0124880 A1 | 5/2009 | Smith |
| 2009/0125007 A1 | 5/2009 | Splinter |
| 2009/0248049 A1 | 10/2009 | Perkins |
| 2009/0281394 A1 | 11/2009 | Russell et al. |
| 2010/0014810 A1 | 1/2010 | Eberle et al. |
| 2010/0087732 A1 | 4/2010 | Eberle et al. |
| 2010/0109104 A1 | 5/2010 | Tlensuu et al. |
| 2010/0113942 A1 | 5/2010 | Eberle |
| 2010/0135111 A1 | 6/2010 | Bates et al. |
| 2010/0152607 A1 | 6/2010 | Kassab |
| 2010/0234698 A1 | 9/2010 | Manstrom et al. |
| 2010/0241008 A1 | 9/2010 | Belleville et al. |
| 2010/0280330 A1 | 11/2010 | Samuelsson et al. |
| 2010/0286536 A1 | 11/2010 | Samuelsson et al. |
| 2010/0286537 A1 | 11/2010 | Pijls |
| 2011/0004198 A1 | 1/2011 | Hoch |
| 2011/0060229 A1 | 3/2011 | Hulvershorn et al. |
| 2011/0066047 A1 | 3/2011 | Belleville et al. |
| 2011/0071407 A1 | 3/2011 | Hubinette et al. |
| 2011/0083521 A1 | 4/2011 | Hollander et al. |
| 2011/0123154 A1 | 5/2011 | Eberle et al. |
| 2011/0137140 A1 | 6/2011 | Tearney et al. |
| 2011/0178383 A1 | 7/2011 | Kassab |
| 2011/0178413 A1 | 7/2011 | Schmitt et al. |
| 2011/0178417 A1 | 7/2011 | Kassab |
| 2011/0196255 A1 | 8/2011 | Kassab |
| 2011/0245693 A1 | 10/2011 | Hastings et al. |
| 2011/0251497 A1 | 10/2011 | Corl et al. |
| 2011/0306867 A1 | 12/2011 | Gopinathan et al. |
| 2011/0319773 A1 | 12/2011 | Kanz et al. |
| 2012/0053918 A1 | 3/2012 | Taylor |
| 2012/0071782 A1 | 3/2012 | Patil et al. |
| 2012/0072190 A1 | 3/2012 | Sharma et al. |
| 2012/0101355 A1 | 4/2012 | Gopinathan et al. |
| 2012/0101369 A1 | 4/2012 | Patil et al. |
| 2012/0108943 A1 | 5/2012 | Bates et al. |
| 2012/0136244 A1 | 5/2012 | Manstrom et al. |
| 2012/0172731 A1 | 7/2012 | Smith |
| 2012/0172732 A1 | 7/2012 | Meyer |
| 2012/0203118 A1 | 8/2012 | Samuelsson et al. |
| 2012/0220836 A1 | 8/2012 | Alpert et al. |
| 2012/0220837 A1 | 8/2012 | Alpert et al. |
| 2012/0220883 A1 | 8/2012 | Manstrom et al. |
| 2012/0227505 A1 | 9/2012 | Belleville et al. |
| 2012/0271178 A1 | 10/2012 | Smith |
| 2012/0278008 A1 | 11/2012 | Davies et al. |
| 2012/0316419 A1 | 12/2012 | Chevalier |
| 2013/0015975 A1 | 1/2013 | Huennekens et al. |
| 2013/0023762 A1 | 1/2013 | Huennekens et al. |

(56) References Cited

U.S. PATENT DOCUMENTS

| | | |
|---|---|---|
| 2013/0023763 A1 | 1/2013 | Huennekens et al. |
| 2013/0046190 A1 | 2/2013 | Davies |
| 2013/0060133 A1 | 3/2013 | Kassab et al. |
| 2013/0090555 A1 | 4/2013 | Kassab |
| 2013/0096409 A1 | 4/2013 | Hiltner et al. |
| 2013/0109980 A1 | 5/2013 | Teo |
| 2013/0116579 A1 | 5/2013 | Svanerudh |
| 2013/0131523 A1 | 5/2013 | Suchecki et al. |
| 2013/0190633 A1 | 7/2013 | Dorando et al. |
| 2013/0216481 A1 | 8/2013 | Rosenmeier |
| 2013/0303914 A1 | 11/2013 | Hiltner et al. |
| 2013/0324864 A1 | 12/2013 | Manstrom et al. |
| 2014/0024235 A1 | 1/2014 | Russell |
| 2014/0024950 A1 | 1/2014 | Hiltner et al. |
| 2014/0086461 A1 | 3/2014 | Yao et al. |
| 2014/0180140 A1 | 6/2014 | Alpert |
| 2014/0180141 A1 | 6/2014 | Millett |
| 2014/0187980 A1 | 7/2014 | Burkett |
| 2014/0187984 A1 | 7/2014 | Burkett |
| 2014/0276142 A1 | 9/2014 | Dorando |
| 2014/0379269 A1 | 12/2014 | Schmitt |
| 2015/0032011 A1 | 1/2015 | McGowan et al. |
| 2015/0074995 A1 | 3/2015 | Patil et al. |
| 2015/0105673 A1 | 4/2015 | Gregorich |
| 2015/0112191 A1 | 4/2015 | Gilboa et al. |
| 2015/0141853 A1 | 5/2015 | Miller et al. |
| 2015/0148693 A1 | 5/2015 | Burkett |
| 2015/0157216 A1 | 6/2015 | Stigall et al. |
| 2015/0173722 A1 | 6/2015 | Huennekens et al. |
| 2015/0265167 A1 | 9/2015 | McGowan et al. |
| 2015/0272449 A1 | 10/2015 | Meyer |
| 2015/0282765 A1 | 10/2015 | Goshen et al. |
| 2015/0313479 A1 | 11/2015 | Stigall et al. |
| 2015/0359438 A1 | 12/2015 | McCaffrey et al. |
| 2015/0359439 A1 | 12/2015 | Manstrom et al. |
| 2016/0022153 A1 | 1/2016 | Dorando |
| 2016/0022956 A1 | 1/2016 | Purdy et al. |
| 2016/0066802 A1 | 3/2016 | Keller |
| 2016/0106321 A1 | 4/2016 | Sharma et al. |

FOREIGN PATENT DOCUMENTS

| | | |
|---|---|---|
| EP | 1658808 | 8/1995 |
| EP | 1260175 | 11/2002 |
| EP | 1419796 | 5/2004 |
| EP | 1493381 | 1/2005 |
| EP | 1514512 | 3/2005 |
| EP | 1702641 | 9/2006 |
| JP | 10033488 | 10/1998 |
| JP | 2000333913 | 12/2000 |
| JP | 2004-194996 | 7/2004 |
| JP | 2005095603 | 4/2005 |
| JP | 20053638066 | 4/2005 |
| JP | 20053705458 | 10/2005 |
| JP | 2006204378 | 8/2006 |
| JP | 10137199 | 5/2010 |
| NL | 2009285 | 8/2012 |
| WO | WO1997/000641 | 1/1997 |
| WO | WO1999/058059 | 11/1999 |
| WO | WO2003/022122 | 3/2003 |
| WO | WO2006/037082 | 4/2006 |
| WO | WO2006/0117154 | 11/2006 |
| WO | WO2011/0120565 | 10/2011 |
| WO | WO2011/0161212 | 12/2011 |
| WO | WO2012/093260 | 7/2012 |
| WO | WO2012/173697 | 12/2012 |
| WO | WO2013/061281 | 5/2013 |
| WO | WO2014/025255 | 2/2014 |
| WO | WO2014/176448 | 10/2014 |
| WO | WO2015/150128 | 10/2015 |
| WO | WO2016/001017 | 1/2016 |

\* cited by examiner

DUAL LUMEN CATHETER FOR PROVIDING A VASCULAR PRESSURE MEASUREMENT

FIELD OF THE INVENTION

The invention relates to a catheter for providing a vascular pressure measurement.

BACKGROUND OF THE INVENTION

The severity of a stenosis or lesion in a blood vessel may be assessed by obtaining proximal and distal pressure measurements relative to the given stenosis and using those measurements for calculating a value of the Fractional Flow Reserve (FFR). FFR is defined as the ratio of a distal pressure measurement ($P_d$) taken on the distal side of the stenosis and a proximal pressure measurement taken on the proximal side of the stenosis usually within the aorta ($P_a$). Conventionally, a sensor placed on the distal portion of a flexible interventional device, such as a guide wire, is utilized to obtain the distal pressure measurement $P_d$, while an external pressure transducer is fluidly connected via tubing to a guide catheter for obtaining the proximal or aortic pressure measurement $P_a$. Calculation of the FFR value provides a lesion specific index of functional severity of the stenosis in order to determine whether the blockage limits blood flow within the vessel to an extent that treatment is needed. An optimal or normal value of FFR in a healthy vessel is 1.00, while values less than about 0.80 are generally deemed significant and in need of an interventional treatment. Common interventional treatment options include balloon angioplasty and/or stent implantation.

Blood flow through the coronary arteries is affected by fluctuations in the pressure arising proximally of the lesion, e.g., in the aorta, as well as fluctuations in pressure arising distally of the lesion, e.g., in the microcirculation. Accordingly, it is not possible to accurately assess the severity of a coronary lesion by simply measuring the pressure differential across the lesion because the pressure measurement taken on the distal side of the lesion is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, such as adenosine, are administered to reduce and stabilize the resistance within the coronary arteries. These vasodilator agents reduce the dramatic fluctuation in resistance to obtain a relatively stable and minimal resistance value.

Although various solutions have been proposed to provide the distal pressure measurement $P_d$ for calculating an FFR value, there remains a need in the art for alternative devices and methods for obtaining pressure measurements suitable for use in calculating an FFR value for a given stenosis.

BRIEF SUMMARY OF THE INVENTION

Embodiments hereof are directed to a catheter for providing a pressure measurement at a vascular lesion. In one embodiment, the catheter includes a handle component having a pressure sensor disposed therein and an elongate tubular shaft coupled to the handle component. The tubular shaft has a blood pressure lumen that extends between proximal and distal ends thereof, and a guidewire lumen for receiving a guidewire therethrough that extends within the blood pressure lumen from a distal side port to a distal tip of the tubular shaft. The blood pressure lumen provides fluid communication between the pressure sensor within the handle component at the proximal end of the tubular shaft and a plurality of sidewall windows at the distal end of the tubular shaft. In a method in accordance herewith, when the catheter is positioned at a target site of the vascular lesion, the blood pressure lumen fills with blood via the plurality of sidewall windows such that the pressure sensor is able to sense a pressure of the blood at the distal end of the tubular shaft.

In another embodiment, the catheter includes an elongate tubular component having a proximal segment, a transition segment, and a distal segment. The proximal segment extends between a proximal end of the tubular component and the transition segment, and the distal segment extends between the transition segment and a distal end of the tubular component. The distal segment includes first and second lumens, wherein the second lumen is configured for receiving a guidewire therethrough and is disposed within at least a portion of the first lumen to extend between a side port in the transition segment of the tubular component and a distal tip opening of the tubular component. A pressure sensor is at least partially disposed within a lumenal space of the transition segment at a proximal end of the first lumen, wherein the first lumen provides fluid communication between the pressure sensor and a plurality of sidewall openings in the distal segment that are positioned adjacent to a distal end of the tubular component. In a method in accordance herewith, when the catheter is positioned at a target site of the vascular lesion the first lumen fills with blood via the plurality of sidewall openings such that the pressure sensor is able to sense a pressure of the blood at the distal end of the tubular component.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of embodiments hereof are in the context of treatment of blood vessels such as the coronary, carotid and renal arteries, the invention may also be used to measure the pressure gradient over heart valves and may also be used in any other body passageways where it is deemed useful. Furthermore, there is no intention to be bound by any expressed or implied theory presented in the preceding technical field, background, brief summary or the following detailed description.

Figure 1:
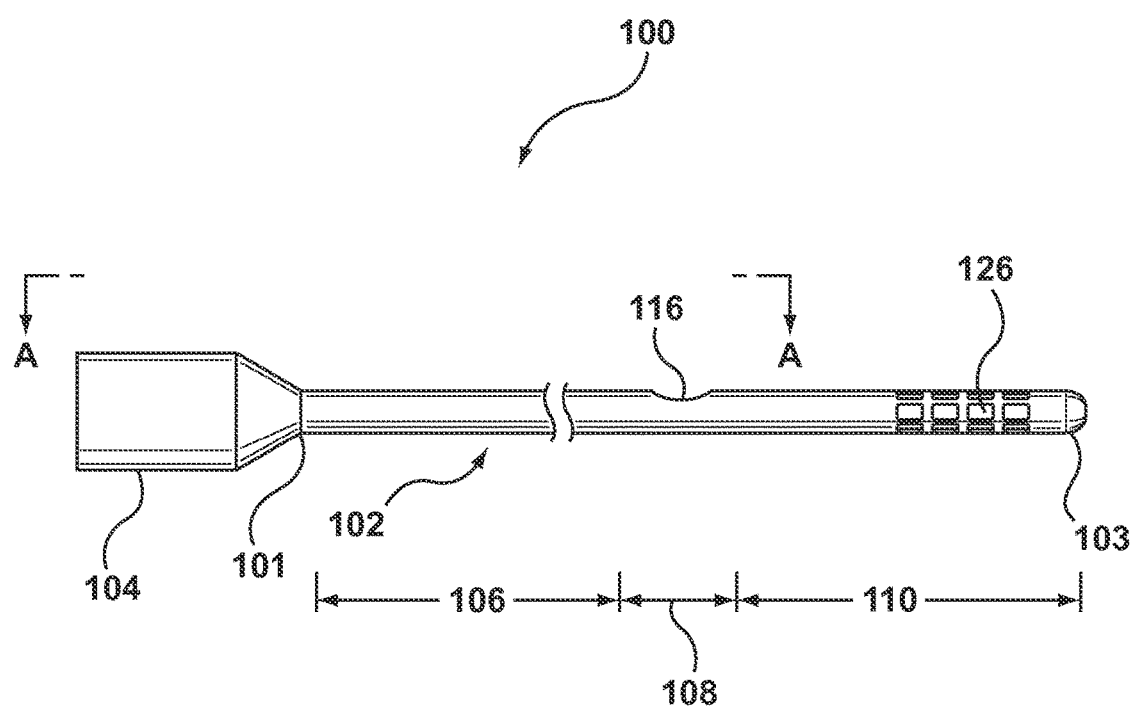
FIG. 1 is a side view of a catheter in accordance with an embodiment hereof.
Figure 1A:
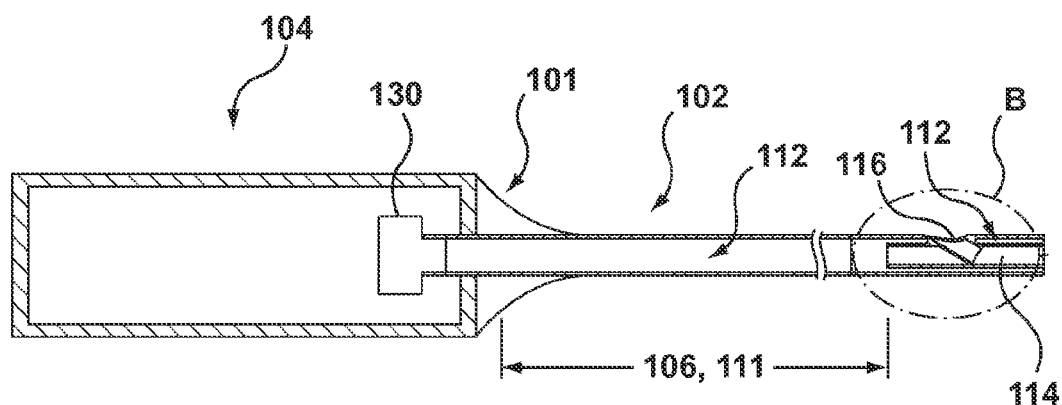
FIG. 1A is a sectional view of the catheter of FIG. 1 taken along line A-A thereof.

FIG. 1 is a side view of a catheter 100 for providing a pressure measurement at a target site of a stenosis or lesion in accordance with an embodiment hereof with FIG. 1A being a sectional view of the catheter taken along line A-A of FIG. 1. Catheter 100 includes an elongate tubular shaft or component 102 having a proximal end 101 and a distal end 103. A handle component 104 is coupled to proximal end 101 of tubular shaft 102 to be accessible for manipulation by a user.

Tubular shaft 102 has a proximal segment 106, a transition segment 108 and a distal segment 110. Proximal segment 106 extends between proximal end 101 and transition segment 108 of the tubular shaft and defines a proximal portion 111 of a first or pressure lumen 112. Pressure lumen proximal end 111 may also be described as longitudinally extending between proximal end 101 and transition segment 108 of the tubular shaft.

Figure 2:
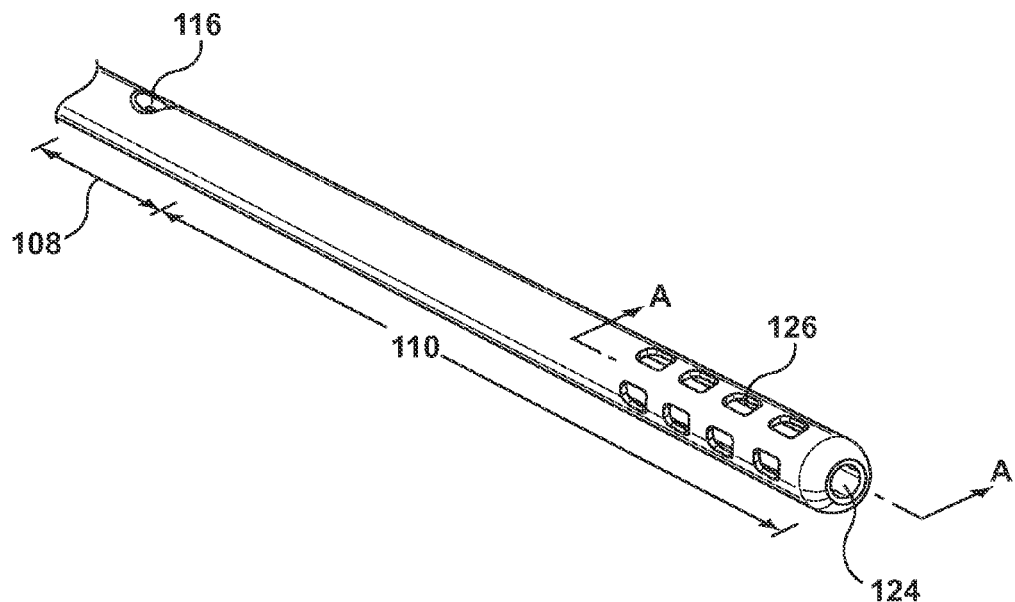
FIG. 2 is a perspective view of a distal portion of the catheter of FIG. 1.

Distal segment 110 extends between transition segment 108 and distal end 103 of the tubular shaft, which is also referred to herein as distal tip 103 of catheter 100. With reference to FIG. 2 that depicts a perspective view of transition and distal segments 108, 110 of catheter 100 and FIG. 2A that depicts a sectional view of a portion of distal segment 110 taken along line A-A of FIG. 2, distal segment 110 includes a polymeric outer tube 120 and a polymeric inner or guidewire tube 122. A distal portion 113 of the first lumen 112 is defined between an inner surface 119 of outer tube 120 and an opposing outer surface 121 of inner tube 122, such that distal portion 113 of first lumen 112 may be described as having an annular cross-section. Inner tube 122 of distal segment 110 defines a second lumen 114 that extends within and is coaxial with the distal portion 113 of first lumen 112. Second lumen 114 is sized to receive a guidewire therethrough and may be referred to as a guidewire lumen. Each of distal portion 113 of first lumen 112 and second lumen 114 may also be described as longitudinally extending between transition segment 108 and tubular shaft distal end 103, with second lumen 114 defining a distal tip opening 124.

Figure 2A:
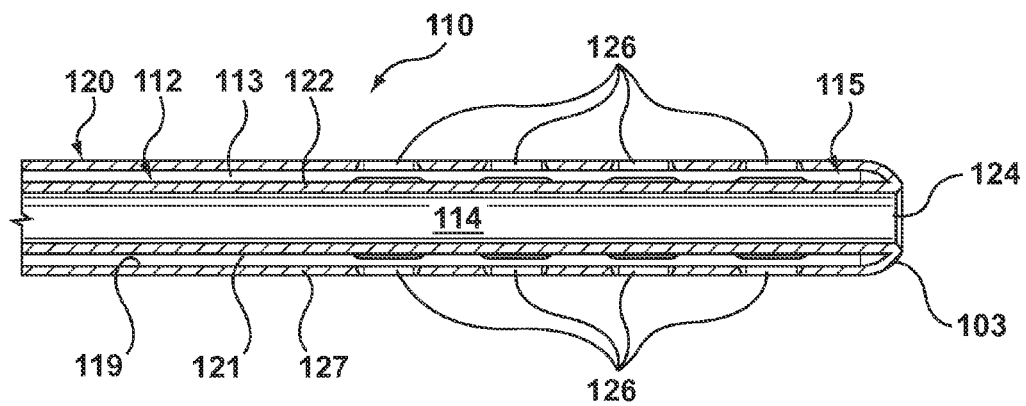
FIG. 2A is a sectional view of the catheter distal portion of FIG. 2 taken along line A-A thereof.

A plurality of openings or windows 126 are formed through a sidewall 127 of distal segment 110 to be in fluid communication with first lumen distal portion 113. As best shown in FIGS. 2 and 2A, a distal end 115 of the annular distal portion 113 of first lumen 112 is closed or capped adjacent to or proximate of distal tip opening 124 such that the only distal access for blood flow into first lumen 112 is provided by distal sidewall openings or windows 126. In an embodiment, distal tip 103 of catheter 100 may be a separate atraumatic tip component that closes or caps distal end 115 of distal portion 113 of first lumen 112. In another embodiment, distal end 115 of distal portion 113 of first lumen 112 may be closed or capped by reflowing the polymers of the inner and outer tubes in the tip region using a laser, hotbox or adhesive.

Figure 2B:
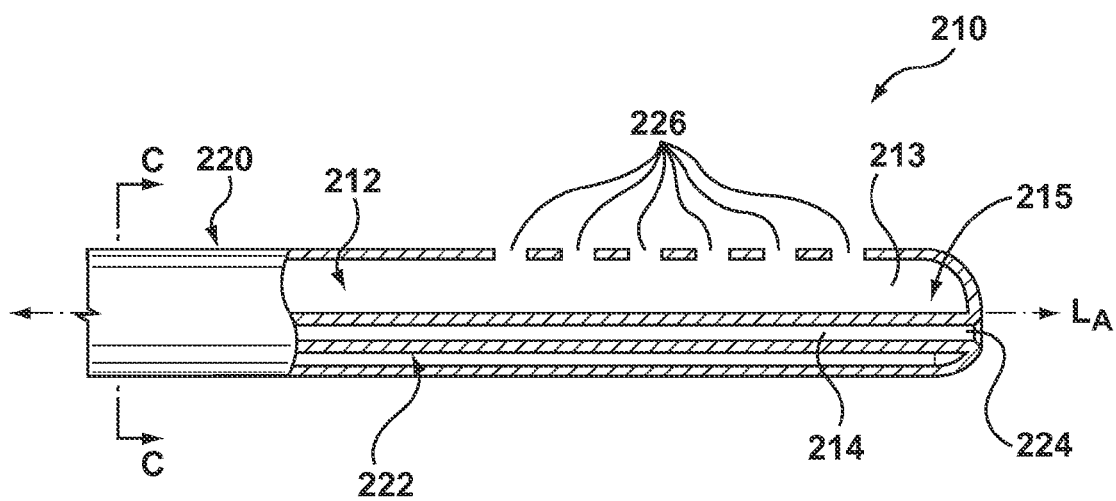
FIG. 2B is a sectional view of a catheter distal portion in accordance with another embodiment hereof.
Figure 2C:
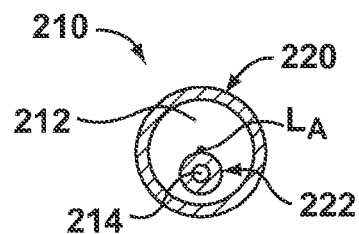
FIG. 2C is a cross-sectional view of the catheter distal portion shown in FIG. 2B taken along line C-C thereof.

In the embodiment shown in FIG. 1, the plurality of sidewall openings 126 are square-shaped apertures that are equally spaced about a circumference of distal segment 110 in equal numbered groups or columns. In another embodiment shown in FIGS. 2B and 2C, a plurality of sidewall openings 226 are not equally spaced about a circumference of a distal segment 210 but instead are formed through one side of an outer tube 220 of distal segment 210 to be in fluid communication with a distal portion 213 of a first lumen 212. As well in the embodiment of FIGS. 2B and 2C, a second lumen 214 defined by an inner tube 222 of distal segment 210 is offset from a longitudinal axis $L_A$ of distal segment 210 such that second lumen 214 is not concentric with the distal portion 213 of the first lumen 212. First lumen 212 is a pressure lumen for receiving blood from the plurality of sidewall openings 226 and fluidly communicating the blood with a proximally placed sensor. Second lumen 214 is sized to receive a guidewire therethrough and may be referred to as a guidewire lumen. A distal end 215 of the annular distal portion 213 of first lumen 212 is closed or capped adjacent to or proximate of a distal tip opening 224 of second lumen 214 such that the only distal access for blood flow into first lumen 212 is provided by the plurality of sidewall openings 226.

Figure 6:
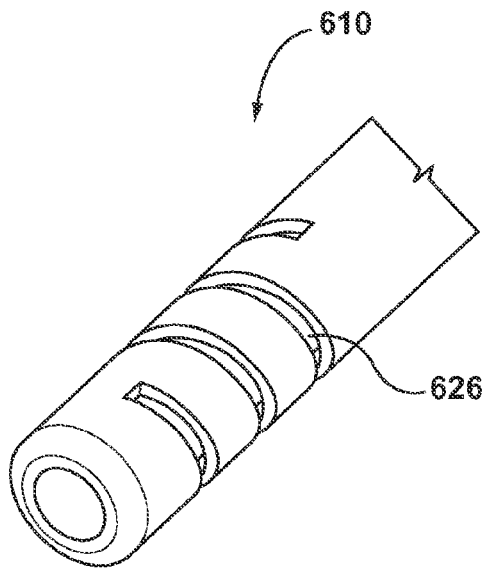
FIG. 6 is a perspective view of a portion of a distal segment of a catheter in accordance with another embodiment hereof.

In other embodiments in accordance herewith, the plurality of sidewall openings may be of any suitable shape, number and size. In another embodiment shown in FIG. 6, a spiral cut 626 within a distal segment 610 of a catheter in accordance herewith may be used to introduce blood into a distal portion of a pressure lumen thereof instead of a plurality of sidewall openings. In an embodiment, all other features of a catheter in accordance with the embodiment of FIG. 6 are similar to features described with reference to the embodiment of FIG. 1. In another embodiment, all other features of a catheter in accordance with the embodiment of FIG. 6 are similar to features described with reference to the embodiment of FIG. 3.

Figure 1B:
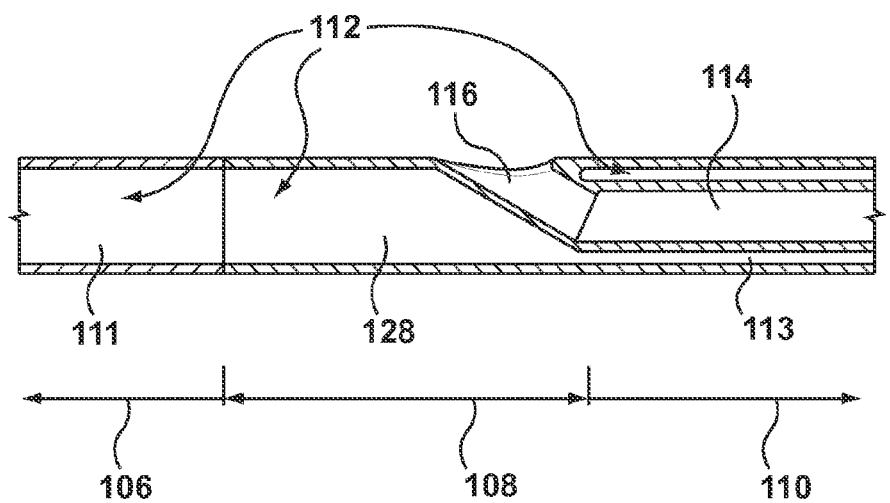
FIG. 1B is an enlarged sectional view of an Area B in FIG. 1A.

With reference to FIG. 1B that depicts an enlarged sectional view of a rapid exchange joint area B of FIG. 1A, transition segment 108 of tubular shaft 102 is so named as it is the portion of catheter 100 in which the single lumen proximal segment 106 of tubular shaft 102 transitions to the dual lumen distal segment 110 of tubular shaft 102. Transition segment 108 is formed to include a distal side port 116, which is sometimes referred to as the rapid exchange joint, and defines a lumenal space 128 that joins proximal and distal portions 111, 113 of first lumen 112. Stated another way as is evident from the foregoing description, transition segment 108 may be considered to longitudinally extend between proximal and distal segments 106, 110 such that lumenal space 128 provides fluid communication between proximal and distal portions 111, 113 of first lumen 112. Side port 116 of catheter 100 is disposed within transition segment 108 and provides access to second lumen 114 and distal tip opening 124 for receiving a guidewire (not shown) therethrough. Accordingly, catheter 100 is a rapid-exchange catheter such that during a minimally invasive percutaneous interventional procedure only the relatively short distal segment 110 thereof is tracked over a guidewire. As well in accordance with embodiments hereof, catheter 100 is a microcatheter having a minimal outer diameter for enabling the catheter to be positioned to cross a stenosis or lesion without undesirably disrupting the blood flow therethrough.

Figure 9:
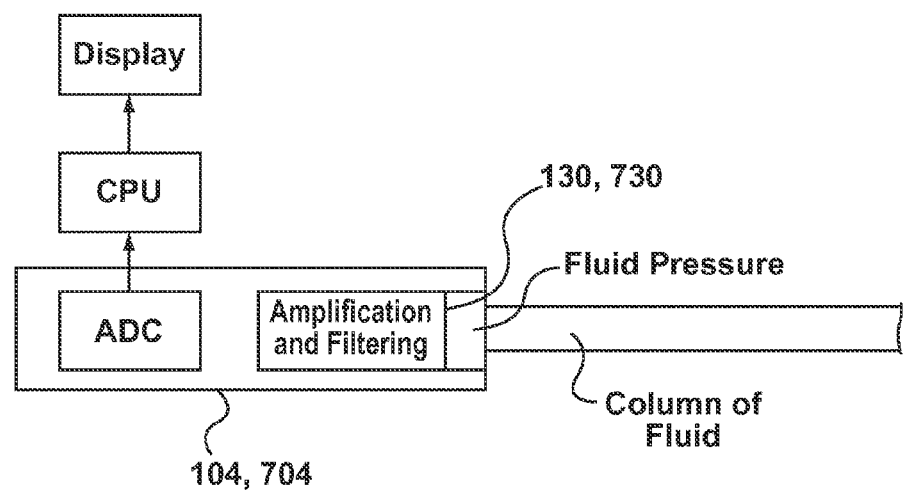
FIG. 9 is a depiction of a pressure sensor in accordance with embodiments hereof communicating with an external CPU and display.

Handle component 104 includes a pressure sensor 130 disposed therein that is in fluid communication with first lumen 112 of tubular shaft 102 as shown in FIG. 1A. As previously discussed, first lumen 112 being comprised of proximal and distal portions 111, 113 and at least a portion of lumenal space 128, extends between proximal and distal ends 101, 103 of tubular shaft 102. As a result, first lumen 112 provides fluid communication between the pressure sensor 130 within handle component 104 at tubular shaft proximal end 101 and the plurality of sidewall openings 126 at tubular shaft distal end 103. In use, when catheter 100 is advanced or tracked to a target site in vivo, first lumen 112 fills with blood at the same pressure as the blood at the catheter tip via the plurality of sidewall openings 126 to thereby enable pressure sensor 130 in handle component 104 to sense a pressure of the blood at the catheter's distal tip 103. In accordance with embodiments hereof, the pressure sensor 130 then communicates the pressure measurement with a CPU and a display device as shown in FIG. 9.

The benefit of having sensor 130 within handle component 104 of catheter 100 for providing a pressure measurement distal of a stenosis rather than having a sensor attached at a distal end of a guidewire, which is the practice in known pressure-sensing guidewires, is that a wider variety of pressure sensors may be used. As well, housing sensor 130 within handle component 104 eliminates the need for the electrical connections of the sensor, such as wires, to extend between the distal end and the proximal end of the catheter, which simplifies and reduces costs of manufacturing the medical device.

Figure 3:
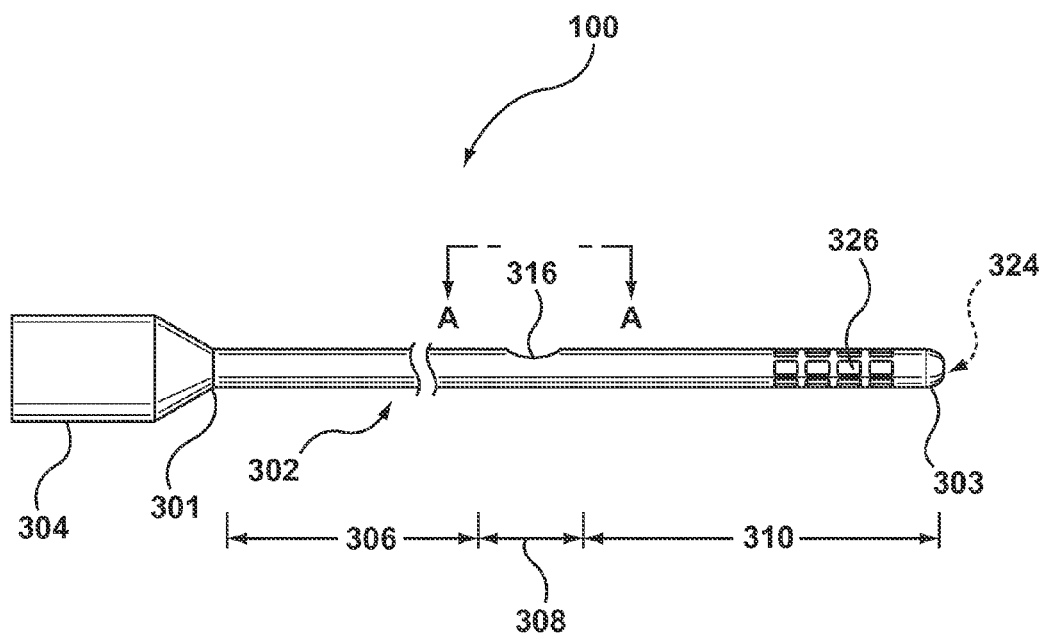
FIG. 3 is a side view of a catheter in accordance with another embodiment hereof.
Figure 3A:
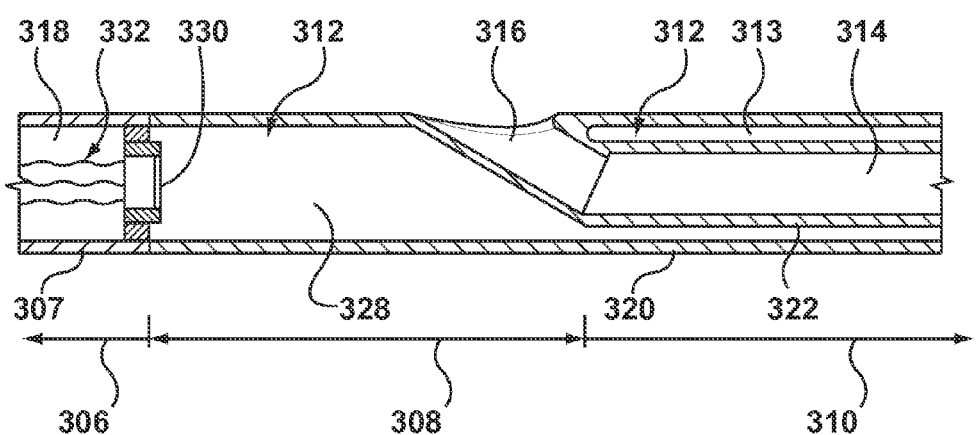
FIG. 3A is a sectional view of the catheter of FIG. 3 taken along line A-A thereof.

FIG. 3 is a side view of a catheter 300 for providing a pressure measurement at a target site of a stenosis or lesion in accordance with another embodiment hereof with FIG. 3A being a sectional view of the catheter taken along line A-A of FIG. 3. Features of catheter 300 that are similar to the same features of catheter 100 will not be further described in detail herein. Catheter 300 includes an elongate tubular component 302 having a proximal end 301 and a distal end 303, which is also referred to herein as distal tip 303 of catheter 300. A handle component 304 is coupled to proximal end 301 of tubular component 302 to be accessible for manipulation by a user. As similarly described with reference to the previous embodiment, tubular component 302 has a proximal segment 306, a transition segment 308, and a distal segment 310, with the proximal segment 306 longitudinally extending between tubular component proximal end 301 and transition segment 308 and with the distal segment 310 longitudinally extending between transition segment 308 and tubular component distal end 303.

In the embodiment of FIG. 3, distal segment 310 of tubular component 302 includes outer tube 320 and inner tube 322. A distal portion 313 of a first or pressure lumen 312 is defined between opposing surfaces of outer and inner tubes 320, 322, such that distal portion 313 of first lumen 312 may be described as having an annular cross-section. Transition segment 308 defines a lumenal space 328 and is formed to include a distal side port 316. Lumenal space 328 of transition segment 308 is the proximal portion of first lumen 312, such that together lumenal space 328 and distal portion 313 form the pressure lumen of catheter 300. Inner tube 322 of distal segment 310 defines a second lumen 314 that extends between side port 316 in transition segment 308 and a distal tip opening 324 of catheter 300. Inner tube 322 may be described as extending within distal portion 313 of first lumen 312. Similar to the previous embodiment, catheter 300 is a rapid exchange catheter with each of side port 316, second lumen 314 and distal tip opening 324 being configured for receiving a guidewire therethrough.

Unlike the previous embodiment in which a pressure sensor is disposed within a handle component of the catheter, a pressure sensor 330 in the embodiment of FIG. 3 is disposed at a distal end 307 of proximal segment 306 to be situated within lumenal space 328 of transition segment 308, which as noted above forms the proximal portion of first lumen 312. In other embodiments, the pressure sensor 330 may be disposed entirely within proximal segment 306 or may be disposed to extend between the proximal and transition segments 306, 308. In the embodiment shown in FIG. 3A, pressure sensor 330 is disposed within transition segment 308 proximal of side port 316 so as to be at or near a proximal end of the transition segment. In order to accommodate electrical connections 332 of pressure sensor 330, proximal segment 306 of tubular component 302 defines a third lumen or electrical conduit 318 that is not in fluid communication with either of first or second lumens 312, 314 but instead is electrically isolated or insulated therefrom. Third lumen 318 is configured for receiving electrical connections 332 of pressure sensor 330 such that the electrical connections may extend through proximal segment 306 to tubular component proximal end 301 and/or handle component 304.

First lumen 312 being comprised of lumenal space 328 and distal portion 313 extends between distal end 307 of proximal segment 306 and the distal end 303 of the catheter, such that first lumen 312 provides fluid communication between pressure sensor 330 and a plurality of sidewall openings or windows 326 in distal segment 310. As similarly described in the previous embodiment with reference to FIGS. 2 and 2A, a distal end (not shown) of the annular distal portion 313 of first lumen 312 is closed or capped adjacent to or proximate of distal tip opening 324 such that the only distal access for blood flow into first lumen 312 is provided by distal sidewall openings or windows 326. In use, when catheter 300 is advanced or tracked to a target site in vivo, first lumen 312 fills with blood at the same pressure as the blood at the catheter tip via the plurality of sidewall openings 326 to thereby enable pressure sensor 330 to sense a pressure of the blood at the catheter distal tip 303.

The benefit of placing sensor 330 proximal of the rapid exchange transition joint, i.e., at a proximal end of transition segment 308 where there is no guidewire lumen, is that a larger variety of pressure sensors may be used than the pressure sensors that are currently known to be attached at a distal end of a pressure-sensing guidewire. As well, housing sensor 330 at the distal end of proximal segment 306 permits electrical connections 332 to extend from the sensor to the proximal end of the catheter within third lumen 318 of proximal segment 306, which simplifies and reduces costs of manufacturing the medical device.

Figure 4:
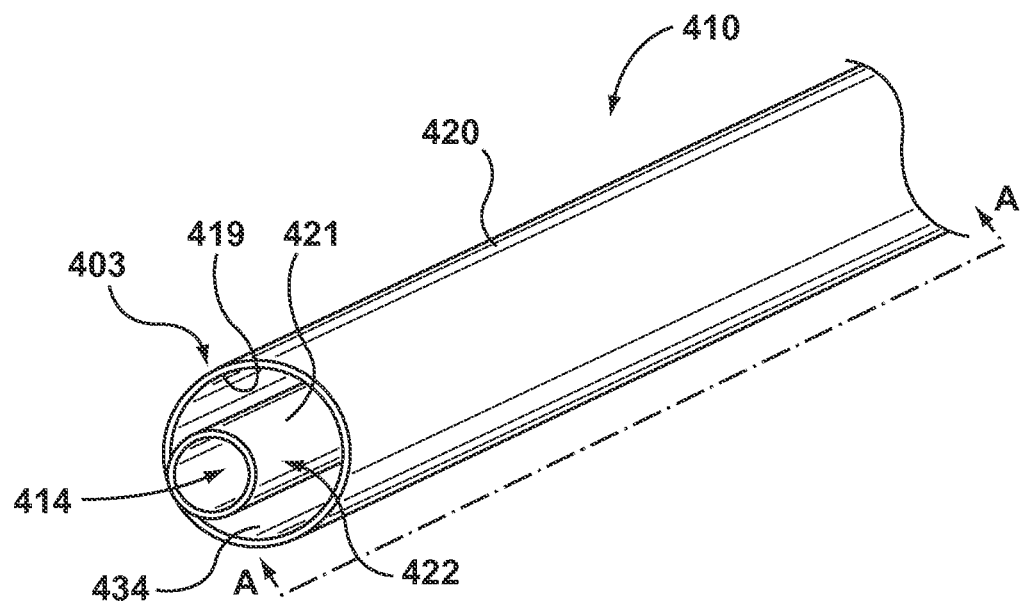
FIG. 4 is a perspective view of a portion of a distal segment of a catheter in accordance with another embodiment hereof.
Figure 4A:
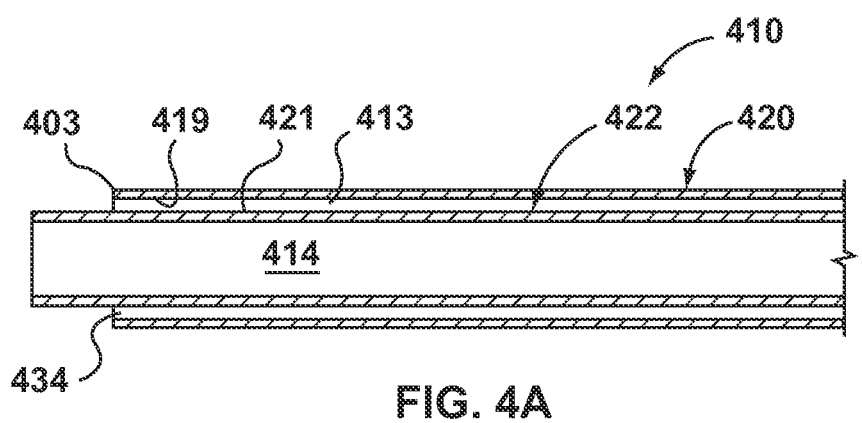
FIG. 4A is a sectional view of the portion of a distal segment of a catheter shown in FIG. 4 taken along line A-A thereof.

In each of the embodiments described above, a distal end of the annular distal portion of the first lumen is closed or capped adjacent to or proximate of the distal tip opening thereof. FIGS. 4 and 4A depict a portion of a distal segment 410 of a tubular component for use in a catheter in accordance with another embodiment hereof in which distal sidewall openings are not utilized. All other features of a catheter in accordance with this embodiment are similar to features described with reference to the previous embodiment and will not be described in detail herein. Distal segment 410 includes outer tube 420 and inner tube 422. Inner tube 422 defines a second lumen 414 that is sized to receive a guidewire therethrough and may be referred to as a guidewire lumen. An annular opening 434 at a distal tip 403 of distal segment 410 is defined between opposing inner and outer surfaces 419, 421 of outer and inner tubes 420, 422, respectively. Annular opening 434 is in fluid communication with a distal portion 413 of a first or pressure lumen of the catheter that is also defined between opposing inner and outer surfaces 419, 421 of outer and inner tubes 420, 422, respectively. In accordance with an embodiment hereof, blood flow from distal tip 403 is fluidly communicated through annular opening 434 and distal portion 413 of the pressure lumen to a pressure sensor situated within a handle component as shown and described in the embodiment of FIG. 1. In accordance with another embodiment hereof, blood flow from distal tip 403 is fluidly communicated through annular opening 434 and distal portion 413 of the pressure lumen to a pressure sensor situated within a transition segment as shown and described in the embodiment of FIG. 3.

Figure 5A:
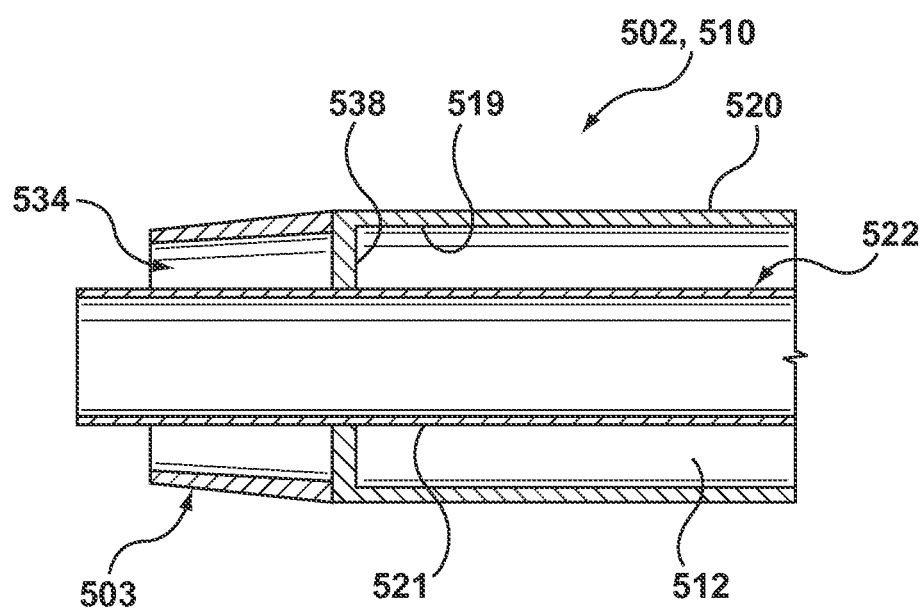
FIGS. 5A and 5B are sectional views of a portion of a distal segment of a catheter in accordance with another embodiment hereof.
Figure 5B:
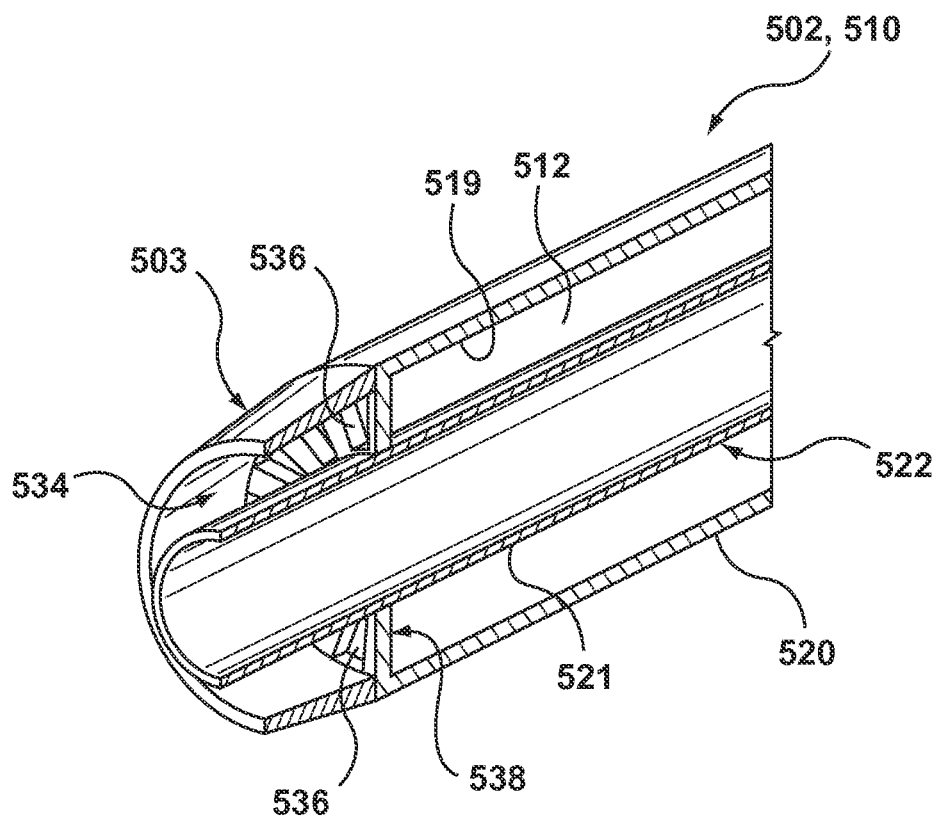

FIGS. 5A and 5B depict a portion of a distal segment 510 of a tubular component 502 for use in a catheter in accordance with another embodiment hereof in which distal sidewall openings are not utilized. All other features of a catheter in accordance with this embodiment are similar to features described with reference to the previous embodiments and will not be described in detail herein. Tubular component 502 includes an annular opening 534 at a distal tip 503 thereof that is defined between opposing inner and outer surfaces 519, 521 of outer and inner tubes 520, 522, respectively, of distal segment 510. Annular opening 534 is in fluid communication with a first or pressure lumen 512 of the catheter. However, unlike the embodiment of FIG. 4, annular opening 534 is in fluid communication with the pressure lumen 512 via a plurality of transverse openings 536 formed within a ring-shaped spacer or support member 538 that is transversely disposed between opposing outer and inner surfaces 519, 521. Although transverse openings 536 are shown in FIG. 5B to have a four-sided polygonal shape, in various other embodiments in accordance herewith the transverse openings may be of any suitable shape, such as squares or circles, may be fewer or greater in number, and/or may be any suitable size or various sizes. In this way during use, blood flow surrounding distal tip 503 is fluidly communicated to first lumen 512, via annular opening 534 and the plurality of transverse opening 536. In accordance with an embodiment hereof, blood within first lumen 512 is fluidly communicated to a pressure sensor situated within a handle component as shown and described in the embodiment of FIG. 1. In accordance with another embodiment hereof, blood within first lumen 512 is fluidly communicated to a pressure sensor situated within a transition segment thereof as shown and described in the embodiment of FIG. 3.

Figure 7:
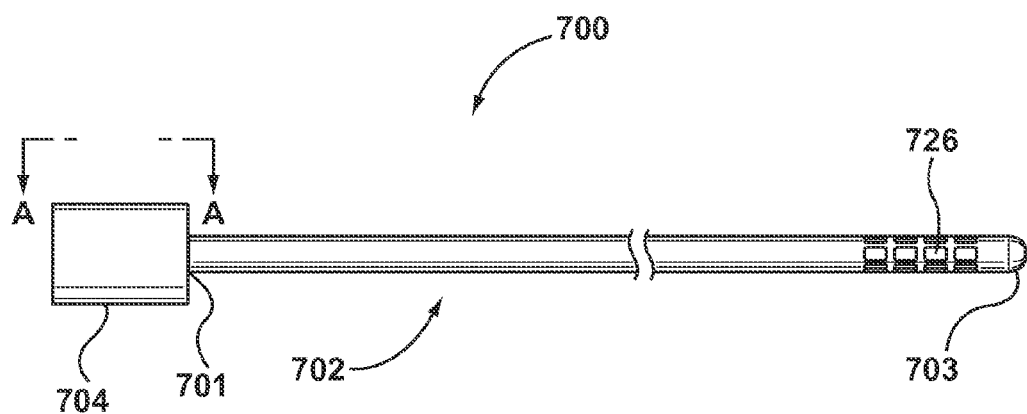
FIG. 7 is a side view of a catheter in accordance with another embodiment hereof.
Figure 7B:
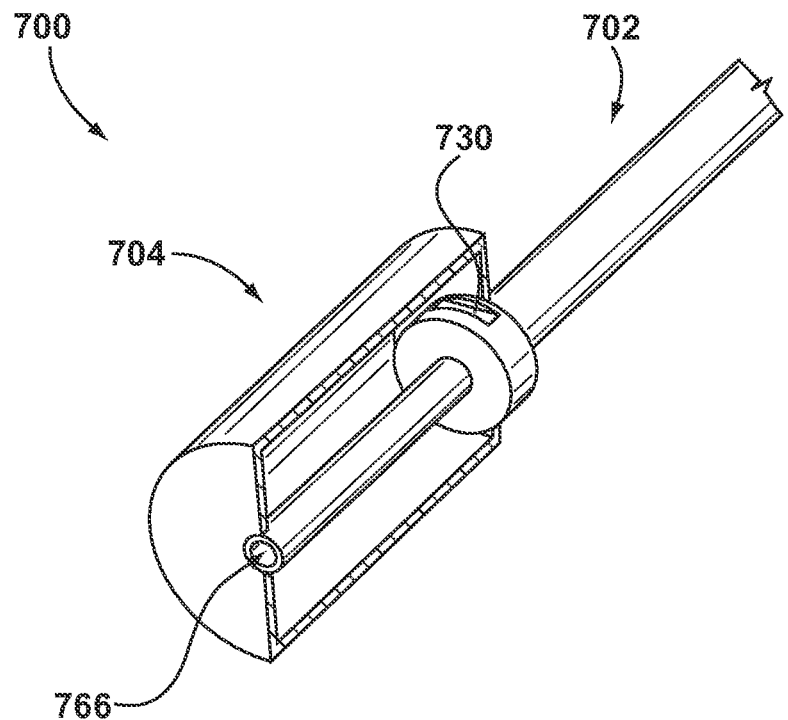
FIG. 7B is a perspective partial sectional view of the handle portion of the catheter of FIG. 7.
Figure 7A:
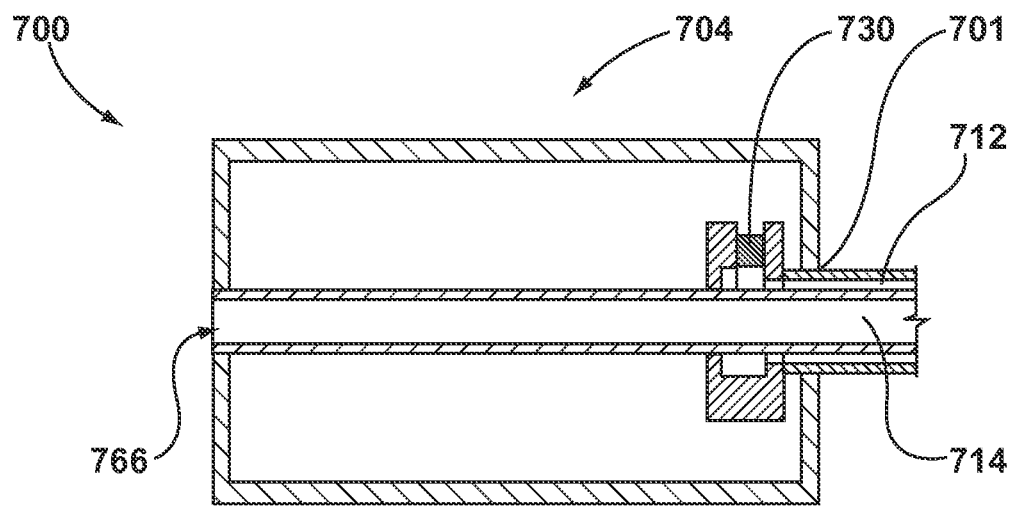
FIG. 7A is a sectional view of a handle portion of the catheter of FIG. 7 taken along line A-A thereof.

FIG. 7 is a side view of a catheter 700 for providing a pressure measurement at a target site of a stenosis or lesion in accordance with another embodiment hereof. FIG. 7A is a sectional view of a handle component 704 of catheter 700 taken along line A-A of FIG. 7. FIG. 7B is a perspective end view of handle portion 704 in partial section. Catheter 700 includes an elongate tubular shaft or component 702 having a proximal end 701 and a distal end 703. Handle component 704 is coupled to proximal end 701 of tubular shaft 702 to be accessible for manipulation by a user.

Tubular shaft 702 is a dual lumen structure having a first or pressure lumen 712 and a second or guidewire lumen 714. Pressure lumen 712 of catheter 700 longitudinally extends between a pressure sensor 730 disposed within handle component 704 and a plurality of sidewall openings 726 disposed proximal of distal end 703 of tubular shaft 702. In contrast to the catheters described in the preceding embodiments, guidewire lumen 714 of catheter 700 extends from a proximal port 766 of handle portion 704 to a distal tip opening (not shown) at distal end 703. Accordingly, catheter 700 may be described as an over-the-wire catheter. In an embodiment, tubular shaft 702 may be comprised of outer and inner tubes with the pressure lumen being defined between opposing surfaces of the outer and inner tubes and with the guidewire lumen being defined by the inner tube. In such an embodiment, the inner tube may be coaxial with the outer tube, as similarly shown in the embodiment of FIG. 2A, or may be offset from a longitudinal axis of the catheter, as similarly shown in FIG. 2B. In another embodiment, tubular shaft 702 may be fully or partially formed from a dual lumen extruded tube with the pressure lumen and the guidewire lumen extending side-by-side along the length or a partial length thereof.

As similarly described in previous embodiments and with particular reference to FIGS. 2 and 2A, a distal end (not shown) of pressure lumen 712 is closed or capped adjacent to or proximate of distal end 703 such that the only distal access for blood flow into pressure lumen 712 is provided by sidewall openings 726. In use, when catheter 700 is advanced or tracked to a target site in vivo, pressure lumen 712 fills with blood at the same pressure as the blood at the distal end 703 of the catheter via the plurality of sidewall openings 726 to thereby enable pressure sensor 730 to sense a pressure of the blood at the catheter distal end 703.

Figure 8:
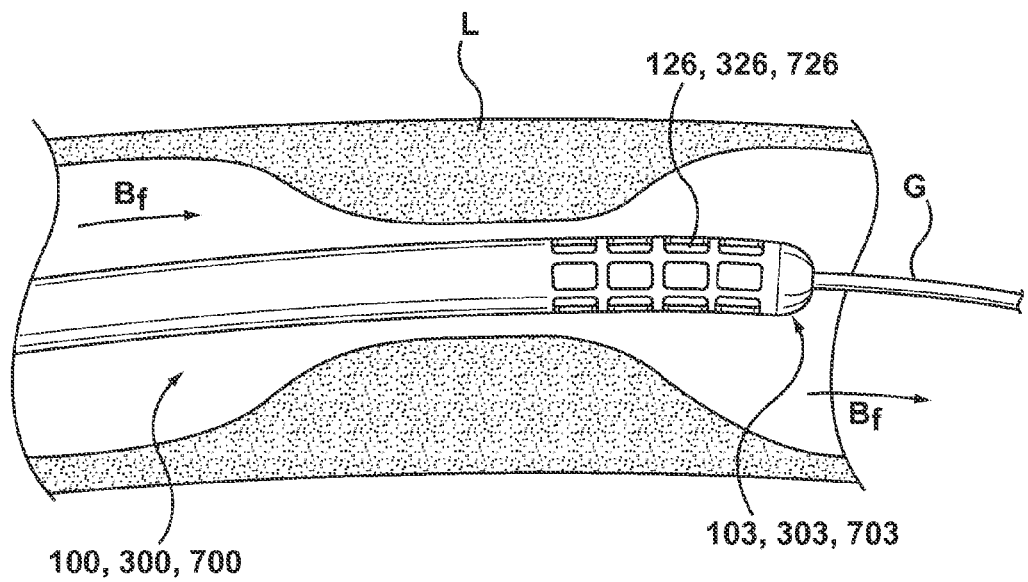
FIG. 8 is a depiction of a distal portion of a catheter in accordance with embodiments hereof positioned across a lesion in the vasculature.

In a method in accordance herewith, a guide catheter (not shown) is tracked through the vasculature until a distal end thereof is disposed within the aorta proximal of an ostium of a branch vessel within which a lesion or stenosis of interest is located. With reference to FIG. 8 that shows blood flow $B_f$ through a portion of a vessel having a lesion L, a guidewire G is advanced through the guide catheter to be disposed across the lesion L. Thereafter, a catheter 100, 300, 700 in accordance with an embodiment hereof is tracked over the indwelling guidewire G to a target site of the lesion L and positioned such that the distal tip 103, 303 and pressure inlet sidewall openings or windows 126, 326, 726 thereof are positioned distal of the lesion as shown in FIG. 8. Accordingly, pressure sensor 130, 330 remains proximal of the lesion L during a distal pressure measurement by catheter 100, 300 700. In one embodiment, adenosine is administered either intracoronary at the site, bolus, or intravenously by continuous infusion for providing an accurate distal pressure measurement ($P_d$) for an FFR value. A proximal pressure measurement $P_a$, which is taken in the aorta by an external AO pressure transducer associated with the guide catheter, and a simultaneous pressure measurement $P_d$ taken with pressure sensor 130, 330, 730 of catheter 100, 300, 700 are then obtained to provide the FFR value, i.e., $P_d/P_a$, for the lesion. Catheter 100, 300, 700 may then be completely withdrawn from the patient or repositioned in vivo at another lesion and the process repeated.

FIG. 9 depicts sensor 130, 730 within handle component 104, 704 communicating a pressure measurement with a CPU and a display device. As previously discussed above, sensor 130, 730 is connected to a pressure lumen of the catheter that fills with a column of blood pressurized to $P_d$. In an embodiment, the sensor 130, 730 communicates the sensed pressure to an amplification and filtering device and thereafter to an analog-to-digital converter (ADC) that communicates with the external CPU and display device. In an alternate embodiment, the CPU may be contained in the handle component or be integrated with the display device. Similar arrangements for communicating a sensed pressure to a CPU and/or display device may be used in handle component 304, with the exception that pressure sensor 330 remains disposed within transition segment 308.

In embodiments hereof, an elongate tubular shaft or component and/or segments thereof may be formed of polymeric materials, non-exhaustive examples of which include polyethylene terephthalate (PET), polypropylene, polyethylene, polyether block amide copolymer (PEBA), polyamide, fluoropolymers, and/or combinations thereof, either laminated, blended or co-extruded. In other embodiments of an elongate tubular shaft or component in accordance herewith, a proximal segment thereof may be a hypotube of a medical grade stainless steel with outer and inner tubes of a distal segment thereof being formed from any of the polymeric materials listed above.

Pressure-sensing catheters in accordance with embodiments hereof may be used for other than providing a distal pressure measurement ($P_d$) for calculating an FFR value. For instance, pressure-sensing catheters in accordance with embodiments hereof may be used to provide an in vivo pressure measurement anywhere along the vasculature, or a particular lesion therein. As well, embodiments hereof may be used to provide an in vivo pressure measurement, at or across a heart valve, venous valve or other valvular location within the body where it may be deemed useful.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A catheter for providing a pressure measurement at a vascular lesion comprising:
    a handle component having a pressure sensor disposed therein;
    an elongate tubular shaft coupled to the handle component, the elongate tubular shaft having a proximal end and a distal end, a first lumen that extends between the proximal end and the distal end, and a second lumen that extends within the first lumen from a distal side port in the elongate tubular shaft to a distal tip of the catheter, wherein the second lumen is at least partially formed by an inner tube extending within the first lumen,
    wherein the first lumen provides fluid communication between the pressure sensor at the proximal end of the elongate tubular shaft and an annular opening at the distal end of the elongate tubular shaft, wherein the annular opening is at the distal tip of the catheter and is defined between an inner surface of the elongate tubular shaft and an outer surface of the inner tube, and wherein the second lumen receives a guidewire therethrough, and
    wherein when the distal tip of the catheter is positioned at a target site of the vascular lesion, the first lumen fills with blood via the annular opening such that the pressure sensor senses a pressure of the blood at the distal tip of the catheter.

2. The catheter of claim 1, wherein the inner tube is a polymeric inner tube secured to extend within the first lumen of the elongate tubular shaft from the distal side port to the distal tip of the catheter.

3. The catheter of claim 1, wherein the elongate tubular shaft further comprises a hypotube from the proximal end to a transition segment of the elongate tubular shaft, the hypotube forming a proximal portion of the first lumen.

4. The catheter of claim 3, wherein the transition segment includes the distal side port.

5. The catheter of claim 1, wherein the pressure sensor remains proximal of the target site during a distal pressure measurement.

6. The catheter of claim 1, wherein the second lumen extends coaxially within the first lumen from the distal side port in the elongate tubular shaft to the distal tip of the catheter.

7. The catheter of claim 1, wherein the second lumen is offset from a longitudinal axis of the first lumen such that the second lumen extends non-coaxially within the first lumen from the distal side port in the elongate tubular shaft to the distal tip of the catheter.

8. A catheter for providing a pressure measurement at a vascular lesion comprising:
    a handle component having a pressure sensor disposed therein;
    an elongate tubular shaft coupled to the handle component, the elongate tubular shaft having a proximal end and a distal end, a first lumen that extends between the proximal and distal ends, and a second lumen that extends within the first lumen from a distal side port in the elongate tubular shaft to a distal tip of the catheter, wherein the second lumen is at least partially formed by a polymeric inner tube secured to extend with the first lumen of the elongate tubular shaft from the distal side port to the distal end of the elongate tubular shaft, the catheter further comprising a ring-shaped spacer transversely disposed between opposing surfaces of the elongate tubular shaft and the inner tube at the distal end of the elongate tubular shaft, wherein one or more openings are in the ring-shaped spacer that is at the distal end of the elongate tubular shaft, wherein the first lumen provides fluid communication between the pressure sensor at the proximal end of the elongate tubular shaft and the one or more openings in the ring-shaped spacer at the distal end of the elongate tubular shaft, and the second lumen receives a guidewire therethrough, and wherein when the distal tip of the catheter is positioned at a target site of the vascular lesion, the first lumen fills with blood via the one or more openings in the ring-shaped spacer such that the pressure sensor senses a pressure of the blood at the distal tip of the catheter.

9. The catheter of claim 1, wherein the elongate tubular shaft has no distal opening in its sidewall.

* * * * *